United States Patent
Arai et al.

(10) Patent No.: US 8,759,553 B2
(45) Date of Patent: Jun. 24, 2014

(54) METHOD FOR PRODUCING EPOXY COMPOUND

(75) Inventors: Yoshikazu Arai, Minato-ku (JP); Hiroshi Uchida, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 13/809,786

(22) PCT Filed: Jun. 29, 2011

(86) PCT No.: PCT/JP2011/064959
§ 371 (c)(1),
(2), (4) Date: Jan. 11, 2013

(87) PCT Pub. No.: WO2012/008308
PCT Pub. Date: Jan. 19, 2012

(65) Prior Publication Data
US 2013/0116455 A1    May 9, 2013

(30) Foreign Application Priority Data
Jul. 14, 2010    (JP) .................................. 2010-159888

(51) Int. Cl.
*C07D 301/12*    (2006.01)
*C07D 301/02*    (2006.01)

(52) U.S. Cl.
USPC ........................................ 549/531; 549/518

(58) Field of Classification Search
USPC ....................................................... 549/518
See application file for complete search history.

(56) References Cited

U.S. PATENT DOCUMENTS

| | | | | |
|---|---|---|---|---|
| 4,021,454 A * | 5/1977 | Wulff et al. | .................. | 549/529 |
| 5,608,088 A | 3/1997 | Watanabe et al. | | |
| 2007/0117993 A1 | 5/2007 | Hori et al. | | |

FOREIGN PATENT DOCUMENTS

| JP | 62-048682 A | 3/1987 |
|---|---|---|
| JP | 08-027136 A | 1/1996 |
| JP | 08-081402 A | 3/1996 |
| JP | 2002-265493 A | 9/2002 |
| JP | 2003-192679 A | 7/2003 |
| JP | 2004-059573 A | 2/2004 |
| JP | 2004-115455 A | 4/2004 |
| JP | 2005-169363 A | 6/2005 |
| JP | 2006-160609 A | 6/2006 |

OTHER PUBLICATIONS

G. B. Payne et al., "Reactions of Hydrogen Peroxide, VII. Akali-Catalyzed Epoxidation and Oxidation Using a Nitrite as Co-reactant", J. Org. Chem., 1991, pp. 659-663, vol. 26, No. 3.
L. A. Arias et al., Epoxidation of Alkenes with Trichloroacetonitrite/Hydrogen Peroxide in a Neutral Biphasic Solvent System, J. Org. Chem., 1983, pp. 888-890, vol. 48, No. 6.
J. E. McIsaac, Jr. et al., "The Mechanism of the Base-Catalyzed Conversion of Nitrites to Amides by Hydrogen Peroxide", J. Org. Chem., 1971, pp. 3048-3050, vol. 36, No. 20.
R. D. Bach et al., "Epoxidation of Olefins by Hydrogen Peroxide-Acetonitrite cis-Cyclocciene Oxide", Organic Synthesis, 1981, pp. 63-66, vol. 60.
Michiel, C A van Vliet et al., "Perfluoroheptadecan-9-one: a Selective and Reusable Catalyst for Epoxidations with Hydrogen Peroxide", Chem. Commun., 1999, pp. 263-264.
International Search Report of PCT/JP2011/064959 dated Sep. 20, 2011.

* cited by examiner

*Primary Examiner* — T. Victor Oh
(74) *Attorney, Agent, or Firm* — Sughrue Mion, PLLC

(57) ABSTRACT

Provided is a safe and simple method for producing an epoxy compound, wherein a compound with a carbon-carbon double bond is epoxidized by using hydrogen peroxide as an oxidizing agent in the presence of acetonitrile, wherein there is no need for concentration of a reaction mixture that contains residual hydrogen peroxide. A method for producing an epoxy compound wherein a compound with a carbon-carbon double bond is epoxidized by using hydrogen peroxide as an oxidizing agent, in the presence of acetonitrile, comprises a first step of adding water and an organic solvent that is incompatible with water and does not dissolve an acetamide by-product of the epoxidation reaction to a reaction mixture, upon completion of the epoxidation reaction, to dissolve the acetamide in the water, a second step of separating an organic layer and an aqueous layer, and a third step of subjecting the organic layer to reduction treatment, and then rinsing and concentrating it to provide an epoxy compound.

18 Claims, No Drawings

METHOD FOR PRODUCING EPOXY COMPOUND

CROSS REFERENCE TO RELATED APPLICATIONS

This application is a National Stage of International Application No. PCT/JP2011/064959 filed Jun. 29, 2011, the contents of which are incorporated herein by reference in their entirety.

TECHNICAL FIELD

The present invention relates to a method for producing an epoxy compound. More specifically, the present invention relates to a method for producing an epoxy compound comprising a post-treatment step of an acetamide by-product (product) from epoxidation of a compound with a carbon-carbon double bond in the presence of acetonitrile, by using hydrogen peroxide as an oxidizing agent.

BACKGROUND ART

Epoxy compounds are used for a variety of purposes, by utilizing a ring-opening of a 1,2-epoxide oxirane ring. In particular, bisphenol A-type epoxy resins and novolak-type epoxy resins are commonly used as semiconductor encapsulating materials, due to their mass productivity and low cost, as well as their excellent heat resistance and water resistance.

The conventionally-known epoxy compounds are mainly produced by reacting phenolic hydroxyl-containing compounds with epihalohydrins. However, epoxy compounds produced by such methods contain organic halogens. From the viewpoint of reliability, it has therefore been difficult to use them as encapsulating materials for highly-integrated semiconductors in recent years. For this reason, great effort is being made toward development of methods for producing halogen-free epoxy compounds, without using epihalohydrins as starting materials, one of which involves oxidation of a carbon-carbon double bond of olefins with oxidizing agents.

Common methods for oxidation of olefins for providing epoxy compounds include methods using heavy metal compounds, or nitric acid, m-chloroperbenzoic acid or the like as oxidizing agents, as well as industrial methods using oxidizing agents, such as peracetic acid or performic acid.

However, since reactions using nitric acid or peracetic acid are dangerous, special equipment is necessary for actual production. Moreover, these oxidizing agents have high oxidizing power and are very dangerous, and several explosions have occurred in the past.

On the other hand, hydrogen peroxide is inexpensive and non-corrosive, and produces either no post-reaction by-products, or only water, and therefore the environmental load is low and it serves as an excellent oxidizing agent for industrial use. Conventional methods that are known for producing epoxy compounds from olefins, by using hydrogen peroxide as an epoxidizing agent, include methods using an aqueous hydrogen peroxide solution for epoxidation in the presence of quaternary ammonium chloride, phosphoric acids and a tungsten metal salt (see Patent documents 1 and 2 below), methods using an aqueous hydrogen peroxide solution for epoxidation with a phase-transfer catalyst, such as a quaternary ammonium salt, with tungstic acids and α-aminomethylphosphonic acid, as catalysts in an organic solvent (see Patent document 3 below), methods of reacting olefins and hydrogen peroxide in a toluene solvent, in the presence of tungstic oxide prepared from a tungsten compound and an aqueous hydrogen peroxide solution, a quaternary ammonium hydrogen sulfate salt and phosphoric acids (see Patent document 4 below), methods of epoxidation using a multicomponent oxidation catalyst comprising a tungsten compound, a quaternary ammonium salt, phosphoric acids and/or boric acids and a hydrogen sulfate salt (see Patent document 5 below), and methods of epoxidation in a chloroform solvent using a catalyst having both phase-transfer capability and epoxidizing capability, such as a cetylpyridinium salt of a heteropolyacid (see Non-Patent document 1 below).

In addition, methods that employ acetonitrile in an epoxidizing reaction using hydrogen peroxide have been known for years (see Non-Patent document 2 below). Since epoxidation by these methods is a milder reaction than conventional methods, and the reaction occurs under a basic condition, there is little decomposition of generated epoxy groups. However, white solid acetamide is generated as a by-product, and it is difficult to separate and remove the acetamide from the target product (epoxy compound). This is because the acetamide and the target product are both organic materials, and thus, if an appropriate solvent is not selected, it may not be possible to remove the acetamide by rinsing. In addition, it is difficult to carry out purification by distillation due to the acetamide being in a solid state at ambient temperature, and scaling-up is difficult in the case of column purification. Furthermore, since the method disclosed in Non-Patent document 2 employs an alcohol-water based reaction solvent, solvent exchange, which is carried out as pretreatment to extract the target epoxy compound product into an organic solvent, makes it necessary to concentrate a reaction mixture while hydrogen peroxide remains therein, and when methanol is used as the solvent, for example, this can potentially lead to concentrating of an organic peroxide derived from hydrogen peroxide, such as methyl peroxide, which results in a very dangerous situation when the process is scaled-up.

PRIOR ART DOCUMENTS

Patent Documents

[Patent document 1] Japanese Unexamined Patent Publication No. 2004-115455
[Patent document 2] Japanese Unexamined Patent Publication No. 2003-192679
[Patent document 3] Japanese Unexamined Patent Publication No. 8-27136
[Patent document 4] Japanese Unexamined Patent Publication No. 2004-59573
[Patent document 5] Japanese Unexamined Patent Publication No. 2005-169363

Non-Patent Documents:

[Non-Patent document 1] Chem. Commun., pp. 263-264 (1999)
[Non-Patent document 2] Organic Synthesis, Vol. 60, pp. 63-66 (1981)

SUMMARY OF THE INVENTION

Problems to be Solved by the Invention

It is an object of the present invention to provide a safe and simple method for producing an epoxy compound, wherein a compound with a carbon-carbon double bond is epoxidized by using hydrogen peroxide as an oxidizing agent in the presence of acetonitrile, the method comprising a post-treatment step in which the target epoxy compound product and an acetamide by-product are separated, the post-treatment step requiring no concentration of a reaction mixture that contains residual hydrogen peroxide.

Means for Solving the Problems

As a result of diligent research and experimentation aimed at achieving the object stated above, the present inventors have found that it is possible to avoid concentrating of hydrogen peroxide, by including the following post-treatment method to remove the acetamide from the target product, and the invention has been completed upon this finding.

Specifically, the present invention provides the following.

[1] A method for producing an epoxy compound wherein a compound with a carbon-carbon double bond is epoxidized by using hydrogen peroxide as an oxidizing agent, in the presence of acetonitrile, the method comprising the following steps:

a first step of adding water and an organic solvent that is incompatible with water and does not dissolve an acetamide by-product of the epoxidation reaction to a reaction mixture, upon completion of the epoxidation reaction, to dissolve the acetamide by-product in the water, a second step of separating an organic layer and an aqueous layer, and a third step of subjecting the organic layer to reduction treatment, and then rinsing and concentrating it to provide an epoxy compound.

[2] The method for producing an epoxy compound according to [1] above, which further comprises, after adding the water and the organic solvent that is incompatible with water and does not dissolve the acetamide by-product of the epoxidation reaction to the reaction mixture in the first step, a step of raising a temperature of the reaction mixture to 30° C. to 40° C.

[3] The method for producing an epoxy compound according to [1] or [2] above, wherein the organic solvent added in the first step is toluene.

[4] The method for producing an epoxy compound according to any one of [1] to [3] above, wherein the compound with a carbon-carbon double bond is an allyl ether compound.

[5] The method for producing an epoxy compound according to [4] above, wherein the compound with a carbon-carbon double bond is an allyl ether compound having two or more allyl ether groups.

[6] The method for producing an epoxy compound according to any one of [1] to [5] above, wherein the reduction treatment in the third step is carried out with a compound selected from the group consisting of an aqueous sodium sulfite solution, an aqueous sodium thiosulfate solution and an aqueous sodium bisulfite solution.

Effect of the Invention

Using the method for producing an epoxy compound according to the invention, it is possible to dissolve acetamide in an aqueous layer and separate the aqueous layer from an organic layer containing the target epoxy compound product, by epoxidizing a compound with a carbon-carbon double bond by using hydrogen peroxide as an oxidizing agent in the presence of acetonitrile, due to adding water and an organic solvent that is incompatible with water and does not dissolve an acetamide by-product of the epoxidation reaction to a reaction mixture after the epoxidation reaction. Therefore, after the aqueous layer is separated, the organic layer alone is subjected to reduction treatment and concentrated, thereby allowing the target epoxy compound to be obtained. The method according to the invention is therefore useful for scaled-up production, since it can reduce concentration of peroxides, compared to conventional methods wherein reduction treatment is carried out after first concentrating and removing solvents containing alcohols and hydrogen peroxide, which are poorly separable from water.

MODE FOR CARRYING OUT THE INVENTION

The method for producing an epoxy compound according to the invention will now be explained in detail.

A method for producing an epoxy compound of the invention, wherein a compound with a carbon-carbon double bond is epoxidized by using hydrogen peroxide as an oxidizing agent in the presence of acetonitrile, the method comprising a first step of adding water and an organic solvent that is incompatible with water and does not dissolve an acetamide by-product of the epoxidation reaction to a reaction mixture, upon completion of the epoxidation reaction, to dissolve substantially all of the acetamide in the water, a second step of separating an organic layer and an aqueous layer, and a third step of subjecting the organic layer to reduction treatment and then rinsing and concentrating it to provide an epoxy compound. In other words, the method for producing an epoxy compound according to the invention comprises a post-treatment after an epoxidation reaction. In the present disclosure, "an organic solvent that is incompatible with water and does not dissolve an acetamide by-product of the epoxidation reaction" is intended to refer to a water-insoluble organic solvent, which has significantly lower solubility for the acetamide by-product than water and undergoes phase separation with water.

According to the invention, hydrogen peroxide is used as the oxidizing agent, and an aqueous hydrogen peroxide solution is preferably used as the hydrogen peroxide source. The concentration of the aqueous hydrogen peroxide solution is not particularly limited, but is generally within the range of 1-80 mass % and preferably 10-60 mass %. From the viewpoint of industrial productivity, and energy cost during separation, a higher concentration of hydrogen peroxide is preferred, but preferably an excessively high concentration and/or an excessively high amount of hydrogen peroxide is not used from the viewpoint of economy and safety.

The amount of the aqueous hydrogen peroxide solution used is not particularly limited. The hydrogen peroxide concentration in the reaction system reduces as the reaction progresses. The hydrogen peroxide in the reaction system is preferably maintained in the range of 1-30 mass % and more preferably 2-10 mass %, by additional replenishment as the concentration reduces. A concentration of below 1 mass % may result in poor productivity, while a concentration of greater than 30 mass % may increase explosibility in the mixed composition of the alcohol and water and thus be dangerous. Since charging a large amount of hydrogen peroxide into the reaction system at the initial stage of the reaction may cause a vigorous reaction to take place which is dangerous, the hydrogen peroxide is preferably added slowly into the reaction system.

The concentration of acetonitrile in the reaction system, used in the method for producing an epoxy compound according to the invention, is controlled so as to be in the range of 0.6 mol/L or greater, and not greater than 2 mol/L or 7 mol/L, during the reaction. The concentration of acetonitrile in the reaction system reduces as the reaction proceeds. If the concentration in the reaction system is below 0.6 mol/L, the yield tends to reduce, while if it exceeds 2 mol/L or 7 mol/L, the epoxidation selectivity of hydrogen peroxide tends to reduce and cost will be undesirably increased.

Therefore, it is preferable that the initial concentration at the start of the reaction is set to within the aforementioned range and the concentration is monitored during the reaction, and the concentration is controlled by further addition not exceeding the upper limit of the range, before the concentration reduces below the lower limit thereof. The concentration is preferably within the range of 1 to 2 mol/L. The total amount of acetonitrile used in the reaction is preferably between 0.6 and 2 times and more preferably between 0.6 and 1.2 times the total amount of hydrogen peroxide used (molar ratio).

The amount of acetonitrile charged at the start of the reaction is preferably in the range of 1.5 to 5 mol equivalents and more preferably 2 to 4 mol equivalents based on the number of double bonds in the compound with a carbon-carbon double bond. At lower than 1.5 mol equivalents, the yield tends to reduce, while at higher than 5 mol equivalents, the epoxidation selectivity of hydrogen peroxide tends to reduce and cost will be undesirably increased. The amount of acetonitrile charged at the start of the reaction is adjusted so as to be at least 0.6 mol/L and not greater than 2 mol/L or 7 mol/L, which is the concentration range in the reaction system during the reaction. The source of the acetonitrile used in the invention is not particularly limited, and it may be a commercial product, or for example, acetonitrile obtained as a by-product during production of acrylonitrile by the Sohio process.

In the method for producing an epoxy compound according to the invention, the pH of the reaction mixture is preferably between 9 and 11, and the pH is more preferably in the range of 9.5 to 11 and even more preferably 10 to 11. If the pH is lower than 9, the reaction rate may reduce, resulting in poor productivity, while if it is higher than 11, the reaction may proceed rapidly, and the yield may undesirably reduce. When a compound with two carbon-carbon double bonds is used as the compound with a carbon-carbon double bond, the diepoxide yield and selectivity will be affected by the pH of the reaction system, and a pH in the range of 10 to 11 is preferred for high diepoxide yield and selectivity.

The basic salt compound used for pH adjustment of the reaction system may be, for example, an inorganic basic salt, such as potassium carbonate, potassium hydrogen carbonate, potassium hydroxide, sodium hydroxide or cesium hydroxide, or an organic basic salt, such as potassium methoxide, potassium ethoxide, sodium methoxide, sodium ethoxide or tetramethylammonium hydroxide. It is preferable that potassium hydroxide and sodium hydroxide are used, since they are highly soluble in water and alcohols, and strongly basic, and are therefore have high reactivity in epoxidation. Potassium carbonate, potassium hydrogen carbonate, potassium hydroxide, sodium hydroxide, potassium methoxide, potassium ethoxide, sodium methoxide and sodium ethoxide are preferred from the viewpoint of easiness in pH adjustment.

The basic salt compounds mentioned above may be used in the form of aqueous solutions or alcohol solutions. Alcohols used as solvents in an alcohol solution include methanol, ethanol, propanol and butanol, and preferably are identical to reaction solvents as described below. The solution of the basic salt compound is preferably added so that the pH of the reaction mixture is not below 9 as the aqueous hydrogen peroxide solution is added, and the temperature of the reaction mixture during the addition is preferably kept within the range of 20° C. to 100° C. and more preferably 25° C. to 60° C.

The reaction temperature in the method for producing an epoxy compound according to the invention is typically in the range of 20° C. to 100° C. and preferably 25° C. to 60° C. In addition, the reaction time depends on the reaction temperature and thus is not uniformly specified for all cases, but is typically in from 4 to 48 hours, preferably 4.5 hours or greater, and not longer than 28 hours or 32 hours.

The substrate to be epoxidized by the method for producing an epoxy compound according to the invention is not particularly limited, so long as it is an organic compound with a carbon-carbon double bond, but is preferably an allyl ether compound. An allyl ether compound is a compound having an allyl ether group (also referred to as an allyloxy group). One or more carbon-carbon double bonds may be present in the compound. Examples of compounds with one carbon-carbon double bond include phenylallyl ether, cresol monoallyl ether, cyclohexene and cyclooctene. Examples of compounds with two or more carbon-carbon double bonds include 3,4-cyclohexenylmethyl-3',4'-cyclohexene carboxylate, allyl ether compounds of novolak-type phenol-based resins, p-diallylaminophenol allyl ether, trimethylolpropane diallyl ether, trimethylolpropane triallyl ether, pentaerythritol diallyl ether, pentaerythritol triallyl ether, pentaerythritol tetraallyl ether, tricyclodecanedimethanol diallyl ether and the like.

As mentioned above, when a compound with a plurality of carbon-carbon double bonds is used, controlling the pH of the reaction mixture in the range of 9 to 11 can provide the corresponding polyepoxide in high yield and selectivity. It is preferable that an aromatic polyallyl ether with an aromatic ring and two or more allyl ether groups is a compound represented by the following general formula:

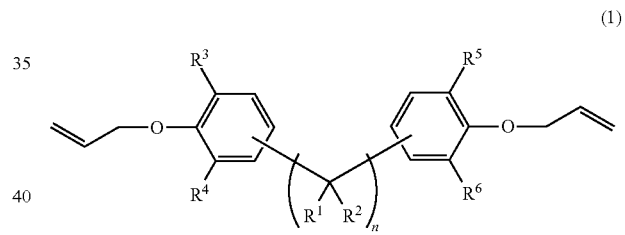

(1)

{wherein $R^1$ and $R^2$ each independently represent hydrogen, a C1-6 alkyl group, a C2-6 alkenyl group, a C3-10 cycloalkyl group or a C6-10 aryl group, or optionally $R^1$ and $R^2$ together form a C2-6 alkylidene group or a C3-12 cycloalkylidene group. $R^3$, $R^4$, $R^5$ and $R^6$ each independently represent hydrogen, a C1-10 alkyl group, a C2-10 alkenyl group, a C3-10 cycloalkyl group or a C6-10 aryl group, and n represents an integer of 0 or 1}. When n is 0, the two benzene rings are directly bonded (forming a biphenyl backbone).

Specific examples of such organic compounds include bisphenol A-type diallyl ethers, such as bisphenol-A diallyl ether, 2,6,2',6'-tetramethylbisphenol-A diallyl ether, 2,2'-diallylbisphenol-A diallyl ether, 2,2'-di-t-butylbisphenol-A diallyl ether and the like, bisphenol F-type diallyl ethers, such as bisphenol-F diallyl ether and the like, and 2,6,2',6'-tetramethylbiphenol diallyl ether, 2,2'-diisopropylbiphenol diallyl ether, 4,4'-ethylidenebisphenol diallyl ether, 4,4'-cyclohexylidenebisphenol diallyl ether, 4,4'-(1-α-methylbenzylidene)bisphenol diallyl ether, 4,4'-(3,3,5-trimethylcyclohexylidene)bisphenol diallyl ether, 4,4'-(1-methyl-benzylidene)bisphenol diallyl ether, 2,2'-dimethylbiphenyl diallyl ether, tetramethylbiphenyl diallyl ether and the like.

Specific examples of aliphatic polyallyl ethers with two allyl ether groups include 1,5-pentanediol diallyl ether, 1,6- hexanediol diallyl ether, 1,9-nonanediol diallyl ether, 1,10-decanediol diallyl ether and neopentylglycol diallyl ether.

Specific examples of alicyclic polyallyl ethers with two allyl ether groups include 1,4-cyclohexanedimethanol diallyl ether and tricyclo[5.2.1.0$^{2,6}$]decanedimethanol diallyl ether.

It is preferable that the substrate to be epoxidized by the method for producing an epoxy compound according to the invention is an aliphatic diallyl ether or alicyclic diallyl ether. Such diallyl ethers can provide the target glycidyl ethers in high yield, since only a few resulting epoxy groups are decomposed when using the method of the invention, compared to epoxidation with hydrogen peroxide by other methods (for example, methods using transition metal catalysts, such as tungsten). In contrast, when an aromatic diallyl ether is used as the substrate, very little decomposition of resulting epoxy groups occurs either in the method of the invention or methods using transition metal catalysts.

Such a reaction substrate can be added to the reaction system without using an organic solvent. However, when an allyl ether with an aromatic ring as the reaction substrate has an excessively high viscosity, the migration speed of hydrogen peroxide to the substrate slows and the reaction rate is affected as well, and therefore it is preferable that the viscosity is reduced by dissolving the substrate in a solvent. Such a solvent is preferably an alcohol, such as methanol, ethanol, propanol or butanol.

When the aforementioned compounds with a carbon-carbon double bond are used as substrates in the method for producing an epoxy compound according to the invention, the concentration of the compound with a carbon-carbon double bond is typically adjusted in the range of at least 0.2 mol/L and not greater than 1.0 mol/L or 2 mol/L, preferably in the range of 0.3 to 0.7 mol/L. If the substrate concentration in the reaction system is less than 0.2 mol/L, the productivity may be impaired, and if it is greater than 1.0 mol/L or 2 mol/L, the yield may be undesirably reduced. Due to the increased compound molecular weight when a compound with 3 or more allyl ether groups is used as the substrate, the substrate concentration may even be below the aforementioned lower limit in such cases.

Considering industrially stable production, it is preferable that the method of epoxidation comprises first charging acetonitrile and the substrate into a reactor, and slowly adding the aqueous hydrogen peroxide solution as its consumption is monitored during the reaction, while the reaction temperature is kept as constant as possible. Applying such a method can reduce accumulation of hydrogen peroxide and minimize pressure increase, even when oxygen gas is generated by abnormal decomposition of hydrogen peroxide in the reactor. Since hydrogen peroxide undergoes active decomposition in a high alkali condition, it is preferable that the pH is adjusted to about 9 to 10 at the initial stage of the reaction, and the pH of the reaction mixture is gradually controlled to about 10 to 11, if necessary, along with addition of hydrogen peroxide.

Upon completion of the epoxidation reaction, the post-treatment step of the invention is carried out. The post-treatment step comprises a first step of adding water and an organic solvent that is incompatible with water and does not dissolve the acetamide by-product of the epoxidation reaction to the reaction mixture, upon completion of the epoxidation reaction, to dissolve substantially all of the acetamide by-product in the water, a second step of separating the organic layer and the aqueous layer, and a third step of subjecting the organic layer to reduction treatment and then rinsing and concentrating it to provide an epoxy compound.

The water added in first step is added in order to dissolve the acetamide by-product that is generated by the epoxidation reaction. The organic solvent that is incompatible with water and does not dissolve acetamide is added in order to dissolve the target epoxy compound product. It is preferable that the organic solvent used is an aromatic organic solvent, such as toluene, benzene or xylene, with toluene being especially preferred, since it does not dissolve acetamide and has high extraction ability for the target epoxy compound. However, the organic solvent is not limited to the aforementioned aromatic organic solvents.

When the water and the organic solvent that is incompatible with water and does not dissolve acetamide are added to the reaction mixture upon completion of the reaction, the ratio of water to organic solvent is not particularly limited, but it is preferable that water/organic solvent (mass ratio) is 0.5 to 2, more preferably 0.8 to 1.3 and even more preferably 0.9 to 1.1, with a ratio of 1 being most preferred. If the ratio of water to organic solvent is less than 0.5, it may not be possible to cleanly separate the two layers, or a longer time may be required. A ratio exceeding 2 corresponds to excessive use of toluene, which is not economical.

The amounts of water and organic solvent added may be, as an example for the ratio specified above, such that water+organic solvent=100 to 600 g and more preferably water+organic solvent=200 to 400 g, for a 1 L scale (when a total amount of starting materials is about 600 g). If the amount is 100 g or less, it may not be possible to sufficiently dissolve the acetamide, thereby rendering separation difficult, while an amount of more than 600 g is economically disadvantageous.

The first step may be carried out with heating, in order to dissolve the acetamide in the aqueous layer in a shorter period of time and reduce the amount of water and organic solvent. The temperature is preferably 30° C. to 50° C. and more preferably 30° C. to 40° C. If it is below 30° C., it may not be possible to completely dissolve the acetamide, and if it is above 50° C., unexpected secondary reactions may occur, such as decomposition of the target epoxy compound.

Next, in the second step, the aqueous layer and organic (solvent) layer are separated. The separation may be carried out by treatment with a conventional separatory funnel. Most of the acetamide and the unreacted acetonitrile and hydrogen peroxide in the reaction mixture are transferred into the aqueous layer, while the target epoxy compound is transferred into the organic (solvent) layer. Then, in the third step, the separated organic layer is subjected to reduction treatment for removal of hydrogen peroxide contained in the organic layer in a small amount, and then to rinsing and concentrating to provide the target epoxy compound. The reduction treatment may be carried out with an aqueous sodium sulfite solution, an aqueous sodium thiosulfate solution or an aqueous sodium bisulfite solution.

EXAMPLES

The present invention is explained in more specific detail by the following examples; however, it should be understood that the invention is in no way limited thereby.

Example 1

After adding 150.0 g (0.67 mol) of 1,4-cyclohexanedimethanol diallyl ether, 109.8 g (2.67 mol) of acetonitrile, 27.7 g (0.2 mol) of potassium carbonate and 200 g of ethanol into a 1 L four-necked flask equipped with a thermometer and a condenser tube, the mixture was stirred at room temperature. Then, 101.1 g (1.34 mol) of a 45% aqueous hydrogen peroxide solution was added dropwise with a dropping funnel over a period of about 3 hours, and by utilizing heat of reaction, the temperature was controlled to maintain a temperature of 35° C. to 25° C. in a water bath. After the dropwise addition, stirring was continued for about 2 hours while maintaining a temperature of 35° C. to 25° C., and another 75.8 g (1.00 mol) of a 45% aqueous hydrogen peroxide solution was added dropwise with a dropping funnel over a period of about 2 hours for reaction while maintaining a temperature of 35° C. to 25° C. Reaction was then conducted for about 24 hours and stirring was terminated. The hydrogen peroxide concentration in the reaction mixture at this time was 0.5%. Next, 200 g of water and 200 g of toluene were added to the reaction mixture and the mixture was heated at 40° C. and stirred. After confirming that all of the precipitated acetamide had dissolved, the mixture was transferred from the reactor to a separatory funnel and the aqueous layer was removed. The hydrogen peroxide concentration in the aqueous layer at this time was 1.5%, with substantially all of the hydrogen peroxide dissolved in the aqueous layer. Thereafter, the organic layer was rinsed 3 times with 100 g of a 5% aqueous sodium sulfite solution and then rinsed twice with 100 g of water, and after confirming, by iodine titration, that the hydrogen peroxide concentration in the waste water after rinsing was not greater than the detection limit, it was determined that no further elution of hydrogen peroxide occurred from the organic layer. Finally, distillation was carried out with an evaporator and vacuum pump to provide the target epoxy compound.

Comparative Example 1

After reaction under the same reaction conditions as in Example 1 (hydrogen peroxide concentration: 0.5%), the reaction mixture was transferred to a 1 L single-necked volumetric flask and concentrated by using an evaporator at 60 mmHg, 35° C. to 40° C., to distill off ethanol and unreacted acetonitrile which are compatible with water. Next, 150 g of toluene was added and extraction was carried out, but the acetamide which was not dissolved remained in the aqueous layer and separation was extremely difficult. Next, the organic layer alone was rinsed 3 times with 100 g of a 5% aqueous sodium sulfite solution and then rinsed twice with 100 g of water, and after confirming, by iodine titration, that the hydrogen peroxide concentration in the waste water after rinsing was not greater than the detection limit, it was determined that no further elution of hydrogen peroxide occurred from the organic layer. Finally, distillation was carried out with an evaporator and vacuum pump to provide the target epoxy compound. Since concentration was accomplished with hydrogen peroxide remaining, unlike Example 1, the risk of concentrating organic peroxides was present, and the process was very dangerous. In addition, Example 1 exhibited superior separability and operativity.

Comparative Example 2

After reaction under the same reaction conditions as Example 1 (hydrogen peroxide concentration: 0.5%), 200 g of a 5% aqueous sodium sulfite solution and 200 g of toluene were added while cooling in a water bath, and the mixture was stirred. A large amount of white solid was precipitated during the stirring, and thus the organic layer and aqueous layer could not be clearly separated. In comparison with Example 1, although reduction treatment could be carried out before concentration, separation of the acetamide by-product was difficult and the process was not realistic for scaling-up.

The invention claimed is:

1. A method for producing an epoxy compound wherein a compound with a carbon-carbon double bond is epoxidized by using hydrogen peroxide as an oxidizing agent, in the presence of acetonitrile, the method comprising conducting an epoxidation reaction and then conducting the following steps:
a first step of adding water and an organic solvent that is incompatible with water and does not dissolve an acetamide by-product of the epoxidation reaction to a reaction mixture, upon completion of the epoxidation reaction, to dissolve the acetamide by-product in the water,
a second step of separating an organic layer and an aqueous layer, and
a third step of subjecting the organic layer to reduction treatment, and then rinsing and concentrating it to provide an epoxy compound.

2. The method for producing an epoxy compound according to claim 1, which further comprises, after adding the water and the organic solvent that is incompatible with water and does not dissolve the acetamide by-product of the epoxidation reaction to the reaction mixture in the first step, a step of raising a temperature of the reaction mixture to 30° C. to 40° C.

3. The method for producing an epoxy compound according to claim 1, wherein the organic solvent added in the first step is toluene.

4. The method for producing an epoxy compound according to claim 1, wherein the compound with a carbon-carbon double bond is an allyl ether compound.

5. The method for producing an epoxy compound according to claim 4, wherein the compound with a carbon-carbon double bond is an allyl ether compound having two or more allyl ether groups.

6. The method for producing an epoxy compound according to claim 1, wherein the reduction treatment in the third step is carried out with a compound selected from the group consisting of an aqueous sodium sulfite solution, an aqueous sodium thiosulfate solution and an aqueous sodium bisulfite solution.

7. The method for producing an epoxy compound according to claim 2, wherein the organic solvent added in the first step is toluene.

8. The method for producing an epoxy compound according to claim 2, wherein the compound with a carbon-carbon double bond is an allyl ether compound.

9. The method for producing an epoxy compound according to claim 3, wherein the compound with a carbon-carbon double bond is an allyl ether compound.

10. The method for producing an epoxy compound according to claim 7, wherein the compound with a carbon-carbon double bond is an allyl ether compound.

11. The method for producing an epoxy compound according to claim 8, wherein the compound with a carbon-carbon double bond is an allyl ether compound having two or more allyl ether groups.

12. The method for producing an epoxy compound according to claim 9, wherein the compound with a carbon-carbon double bond is an allyl ether compound having two or more allyl ether groups.

13. The method for producing an epoxy compound according to claim 10, wherein the compound with a carbon-carbon double bond is an allyl ether compound having two or more allyl ether groups.

14. The method for producing an epoxy compound according to claim 2, wherein the reduction treatment in the third step is carried out with a compound selected from the group consisting of an aqueous sodium sulfite solution, an aqueous sodium thiosulfate solution and an aqueous sodium bisulfite solution.

15. The method for producing an epoxy compound according to claim 3, wherein the reduction treatment in the third step is carried out with a compound selected from the group consisting of an aqueous sodium sulfite solution, an aqueous sodium thiosulfate solution and an aqueous sodium bisulfite solution.

16. The method for producing an epoxy compound according to claim 4, wherein the reduction treatment in the third step is carried out with a compound selected from the group consisting of an aqueous sodium sulfite solution, an aqueous sodium thiosulfate solution and an aqueous sodium bisulfite solution.

17. The method for producing an epoxy compound according to claim 5, wherein the reduction treatment in the third step is carried out with a compound selected from the group consisting of an aqueous sodium sulfite solution, an aqueous sodium thiosulfate solution and an aqueous sodium bisulfite solution.

18. The method for producing an epoxy compound according to claim 7, wherein the reduction treatment in the third step is carried out with a compound selected from the group consisting of an aqueous sodium sulfite solution, an aqueous sodium thiosulfate solution and an aqueous sodium bisulfite solution.

* * * * *